(12) United States Patent
Islava (10) Patent No.: US 10,245,174 B2
(45) Date of Patent: Apr. 2, 2019

(54) VACUUM SPLINT APPARATUS AND METHOD FOR USING THE SAME

(71) Applicant: Care 2 Innovations, Inc., Newport Beach, CA (US)

(72) Inventor: Steve Islava, Newport Beach, CA (US)

(*) Notice: Subject to any disclaimer, the term of this patent is extended or adjusted under 35 U.S.C. 154(b) by 536 days.

(21) Appl. No.: 14/962,862

(22) Filed: Dec. 8, 2015

(65) Prior Publication Data
US 2017/0156912 A1    Jun. 8, 2017

(51) Int. Cl.
| A61F 5/055 | (2006.01) |
| A61F 5/058 | (2006.01) |
| F04B 33/00 | (2006.01) |
| F04B 45/02 | (2006.01) |
| F04B 53/10 | (2006.01) |

(52) U.S. Cl.
CPC .......... *A61F 5/05833* (2013.01); *A61F 5/055* (2013.01); *F04B 33/00* (2013.01); *F04B 45/02* (2013.01); *F04B 53/10* (2013.01)

(58) Field of Classification Search
CPC .......... A61F 13/12; A61F 5/012; A61F 5/055; A61F 5/05883; A61F 5/028; A61F 5/05816; A42B 3/0473; A61H 9/0078
See application file for complete search history.

(56) References Cited

U.S. PATENT DOCUMENTS

| D261,430 S | 10/1981 | Baturin | |
| 5,916,185 A * | 6/1999 | Chitwood | A61F 5/04 602/13 |
| 2006/0155227 A1 | 7/2006 | Daugherty | |
| 2007/0066922 A1 * | 3/2007 | Farley | A61F 5/012 602/18 |
| 2009/0234263 A1 * | 9/2009 | Doel | A61F 5/05816 602/13 |
| 2010/0121243 A1 * | 5/2010 | Aune, Jr. | A61H 1/0296 602/32 |
| 2012/0277644 A1 | 11/2012 | Williams | |

* cited by examiner

*Primary Examiner* — Ophelia A Hawthorne
(74) *Attorney, Agent, or Firm* — Marcus C. Dawes; Daniel L. Dawes (57) ABSTRACT

A particle filled neck brace is used for immobilizing the neck of a patient and includes a single handedly operable vacuum hand pump disposed on the neck brace, which pump is communicated to the interior of the neck brace. After the neck brace is secured around the neck of the patient, the vacuum hand pump is manipulated to remove air from the neck brace to form a rigid mold about the patient's neck. The vacuum hand pump has a one way directional valve so that the neck brace remains in a rigid configuration for as long as the neck brace is applied to the patient. The vacuum hand pump also includes a plurality of springs which assist the user in completing a vacuum pump cycle. To release the neck brace, the user opens a release valve which allows ambient air to refill the neck brace and increase its flexibility.

19 Claims, 9 Drawing Sheets

VACUUM SPLINT APPARATUS AND METHOD FOR USING THE SAME

BACKGROUND

Field of the Technology

The invention relates to the field of pneumatic splints, specifically a vacuum operated splint for immobilizing the neck of a patient.

Description of the Prior Art

Medical splints and other immobilizers have long been used to immobilize or otherwise restrict the physical movement of a region or limb of an injured patient. Many traditional splints are made from cardboard, plastic, padded board, or fiberglass and may either be generic in shape or specifically formed to fit a specified limb or body part of the patient. Typically, the splint is placed under the injured portion of the patient and is then tightened to straighten and/or immobilize the body part to prevent further relative movement of the body part and thus prevent further injury and allow the patient an opportunity to heal. Some splints include vacuum or pneumatic pumps which inflate the splint with air until a tight hold is achieved around the injured portion of the patient.

A type of splint that is made to fit a specific body part is the neck brace, which is specifically shaped and formed to fit about the neck of the patients while also accommodating their shoulders and face. The most basic neck brace is the soft collar which consists of a section of soft foam that wraps around the neck of the patient and is then held in place with a temporary means of coupling such as Velcro and the like. Other neck braces comprise a semi-rigid plastic frame with a soft inner foam padding which is likewise placed around the injured patient's neck and then held in place with interlocking straps or a sliding or telescopic track element.

A problem with many neck braces, however, is that many of them must be adjusted before being applied to the patient's neck. Therefore before the patient's neck can be immobilized, the person applying the brace must first assess the patient and then manipulate the brace in order to ensure that an appropriate fit is achieved when placed around the patient's neck. This can be critical in emergency situations when an EMT or other medical responder first arrives at an accident scene when every second counts. Inflatable neck braces do not require any pre-adjustment according to size however they do require the coupling and activation of an external pump device before the patient may be sufficiently immobilized. Again, in emergency situations when time and physical access to the injured patient may be limited, such an inflatable neck brace could prove to be more detrimental to the treatment of the patient than other braces.

What is needed therefore is a neck brace which can be easily and quickly applied to an injured patient of any size, which does not require any external pumps for operation and which also properly immobilizes the neck of the patient and prevents for further injury.

BRIEF SUMMARY

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
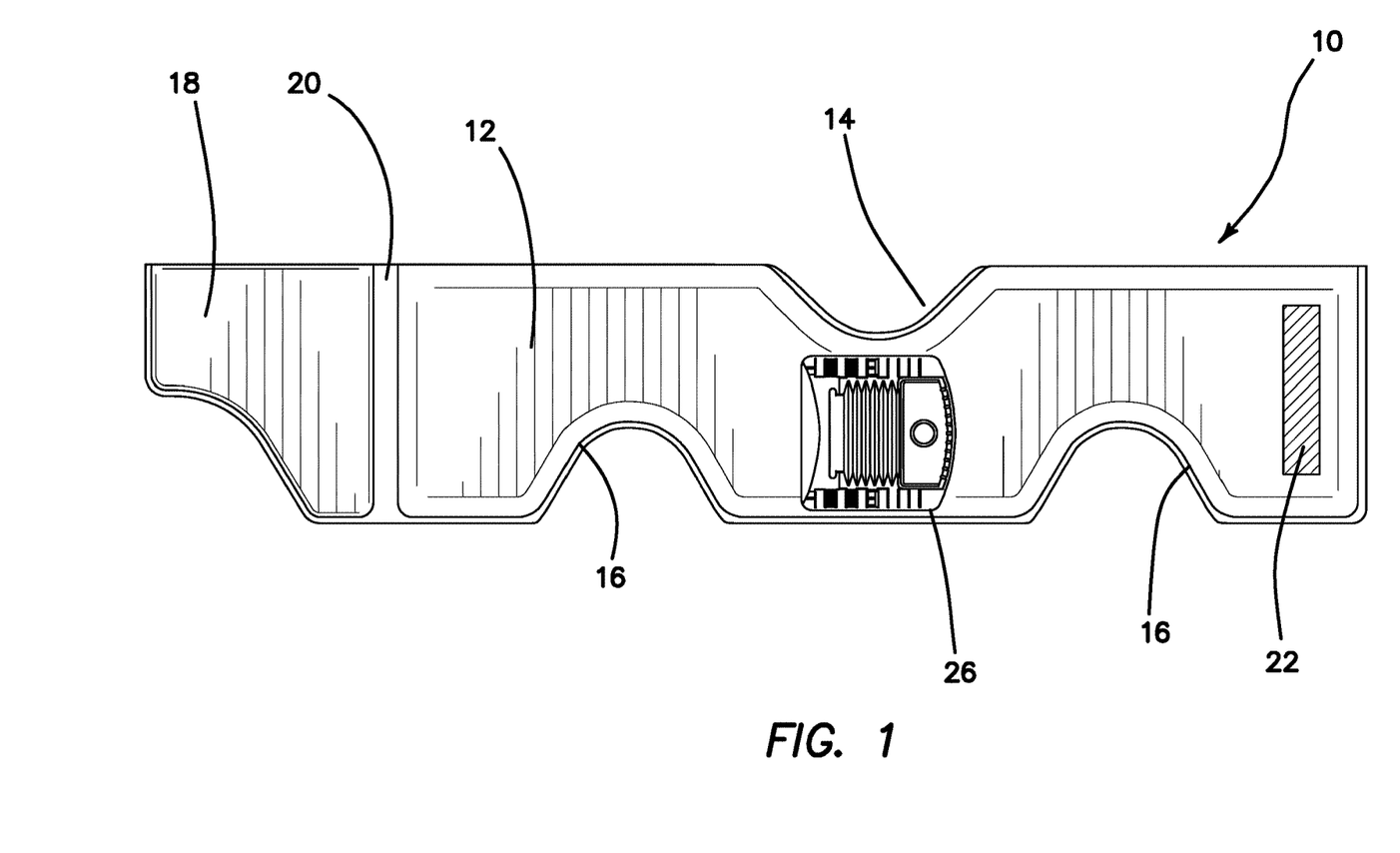
FIG. 1 is a frontal plan view of the neck brace of the illustrated embodiments of the current invention.
Figure 2:
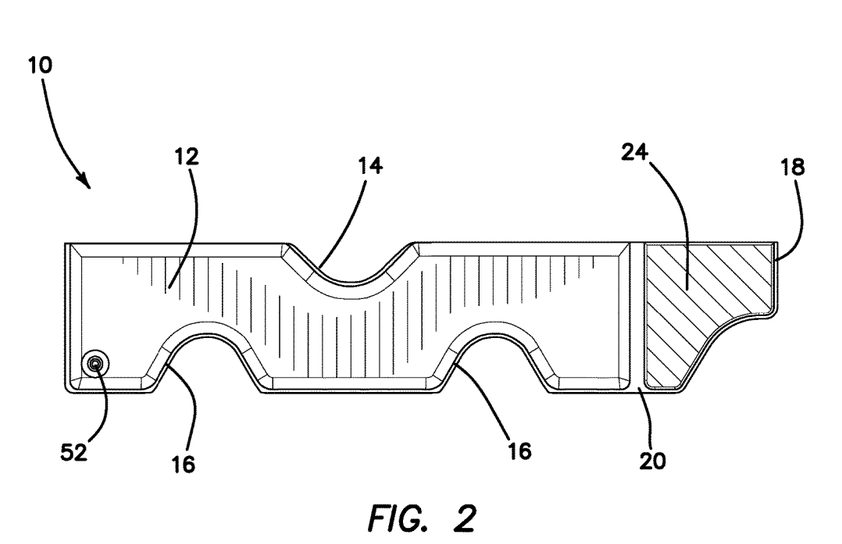
FIG. 2 is a rear plan view of the neck brace seen in FIG. 1.

Greater detail of the illustrated embodiments of the current invention may be had by turning to FIGS. 1 and 2 which shows the current neck brace denoted generally by reference numeral 10. FIG. 1 shows a frontal view of the brace 10 which comprises of a body 12 that is substantially rectangular in shape. The body 12 itself comprises a neck cutout 14 and a plurality of shoulder cutouts 16. The neck cutout 14 and shoulder cutouts 16 are sized and defined in the body 12 at the appropriate locations so that when the neck brace 10 is applied to a patient's neck region, the neck cutout 14 appropriately accommodates the jaw and head of the patient while the shoulder cutouts 16 accommodate the shoulders and chest region of the patient as is known in the art. The body 12 itself is comprised of soft vinyl or other flexible material and is filled with a plurality of foam micro beads known in the art.

The body 12 further comprises a coupling portion 18 joined to the remainder of the body 12 via a flexible region 20. Like the main part of the body 12, the coupling portion 18 is also filled with a plurality of foam micro beads. The flexible region 20 however does not have any micro beads.

The coupling portion 18 is used to join the opposing ends of the body 12 together when the neck brace 10 is placed around the neck of the injured patient. Specifically, as seen in the rear view of the neck brace 10 in FIG. 2, the back surface of the coupling portion 18 comprises a hook and latch fabric pad 24 so that when the neck brace 10 is placed on the patient, the coupling portion 18 is brought around to the opposing end of the front of the body 12 where an opposing hook and latch fabric pad 22 is disposed. The medical professional secures the neck brace 10 in place by aligning the hook and latch fabric pad 24 on the back surface with the opposing pad 22 on the front surface and adhering the pad 24 and opposing pad 22 together. The pads 24, 22 are brought together relative to one another according to the width or circumference of the patient's neck and shoulder region. To release the neck brace 10, the coupling portion 18 is pulled away from the patient which in turn pulls the pad 24 away from the opposing pad 22 of hook and latch fabric thus releasing the ends of the body 12 from each other. With the opposing ends of the body 12 separated, the neck brace 10 may be removed from the neck and shoulder region of the patient.

Figure 3:
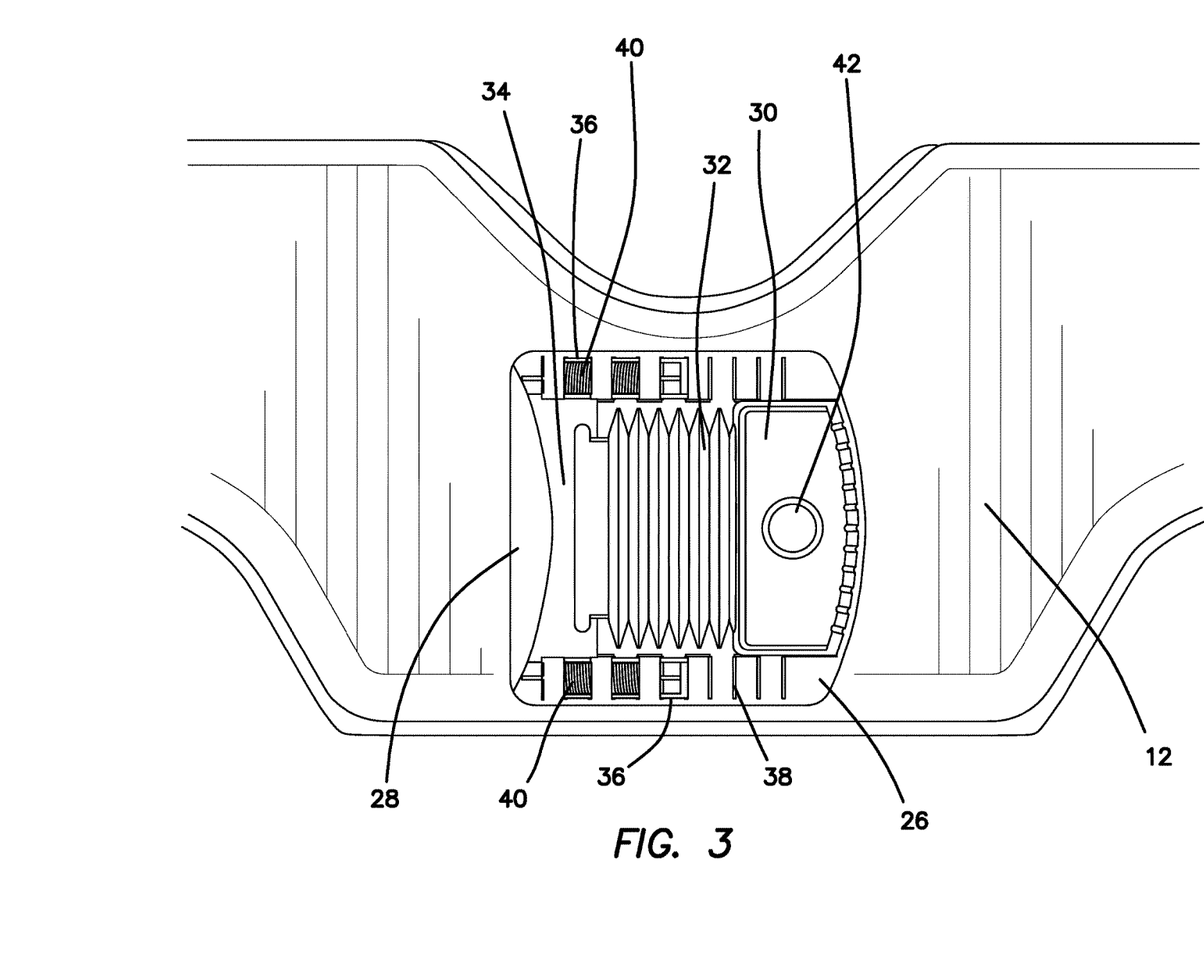
FIG. 3 is a magnified view of a hand pump disposed on a body portion of the neck brace seen in FIG. 1.

Also seen in FIG. 1 is a vacuum hand pump 26 which is disposed on the front surface of the body 12. While the vacuum hand pump 26 is shown as being disposed substantially beneath the neck cutout 14, it is to be expressly understood that the vacuum hand pump 26 may located anywhere on the body 12 of the neck brace 10 without changing the overall function or scope of the claimed invention. Greater detail of the vacuum hand pump 26 may be seen in the magnified views of FIGS. 3 and 4. The vacuum hand pump 26 comprises a housing 30 with a frame 28 disposed around it. Coupled to the housing 30 is a bellows 32 which may be compressed against the housing 30 as detailed further below. Coupled to a distal end of the bellows 32 is a plunger 34. The plunger 34 is sufficiently sized and shaped so that a medical professional may easily grip and press the plunger 34 with his or her fingers. The plunger 34 itself comprises a shuttle 36 disposed on either lateral side of the plunger 34. Each shuttle 36 is disposed in a corresponding track 38 formed within the lateral sides of the frame 28. Also disposed in each track 38 is a tension spring 40 which is coupled to the frame 28 at one end and coupled to the shuttle 36 at the opposing end.

Figure 6:
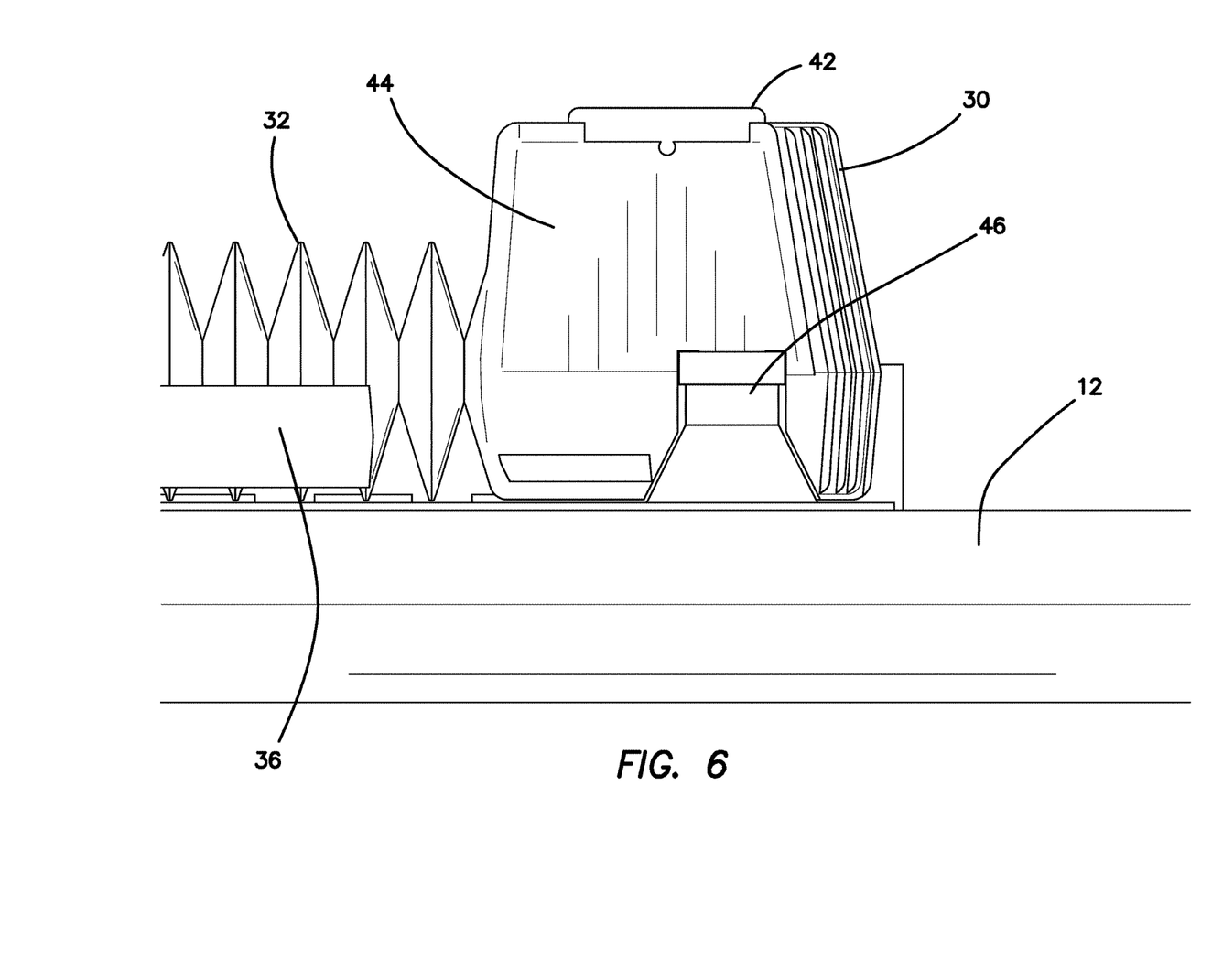
FIG. 6 is a magnified cross sectional view of the vacuum hand pump seen in FIG. 3, including the housing portion of the hand pump.
Figure 9:
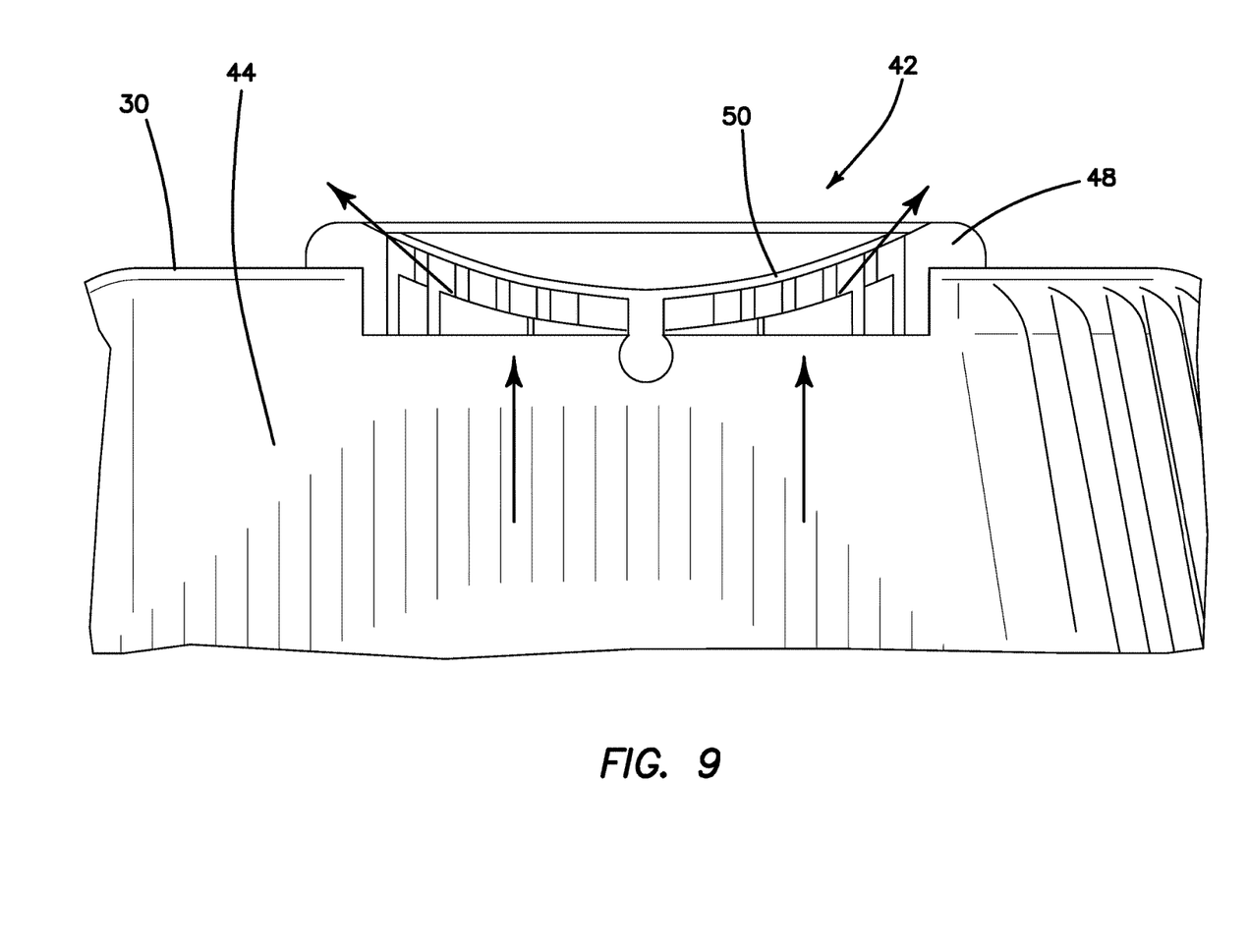
FIG. 9 is a magnified cross sectional view of a one-way directional valve disposed in a surface of the housing seen in FIG. 6.

Greater detail of the housing 30 and the components contained therein may be seen in FIG. 6. The housing 30 comprises an internal chamber 44 for passing a volume of air from the body 12 of the neck brace 10 to the outside environment. Also disposed within the housing 30 is a body valve 46 which is fluidly coupled to an internal volume of the body 12. As is known in the art, the body valve 46 is a one-way directional valve which allows for air to flow in substantially only one direction, namely from the body 12 to the internal chamber 44 of the housing 30. Disposed in the top surface of the housing 30 is a housing valve 42, which like the body valve 46, is a one-way directional valve which allows air to flow in only one direction from the internal chamber 44 of the housing 30 to the ambient environment. Detail of the housing valve 42 may been seen in FIG. 9 which shows the housing valve 42 comprising a substantially annular or ring shaped valve seat 48 and a flexible diaphragm 50. As seen in the cross sectional view of FIG. 9, the diaphragm 50 is disposed within the center of the valve seat 48 with outer circumference of the diaphragm 50 resting on an inner radius of the valve seat 48.

Figure 4:
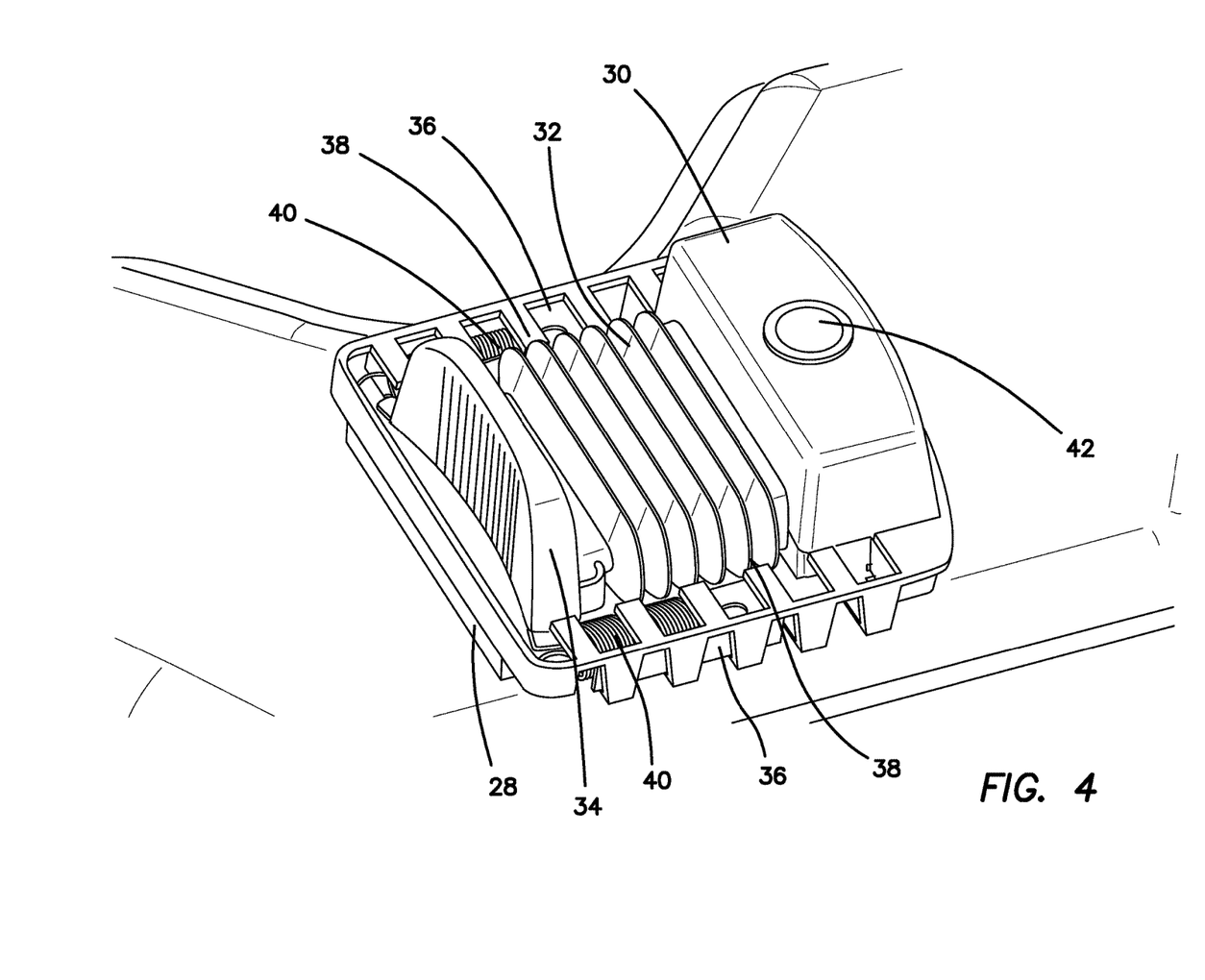
FIG. 4 is a perspective view of the vacuum hand pump disposed on the neck brace when the hand pump is in an expanded configuration.
Figure 5:
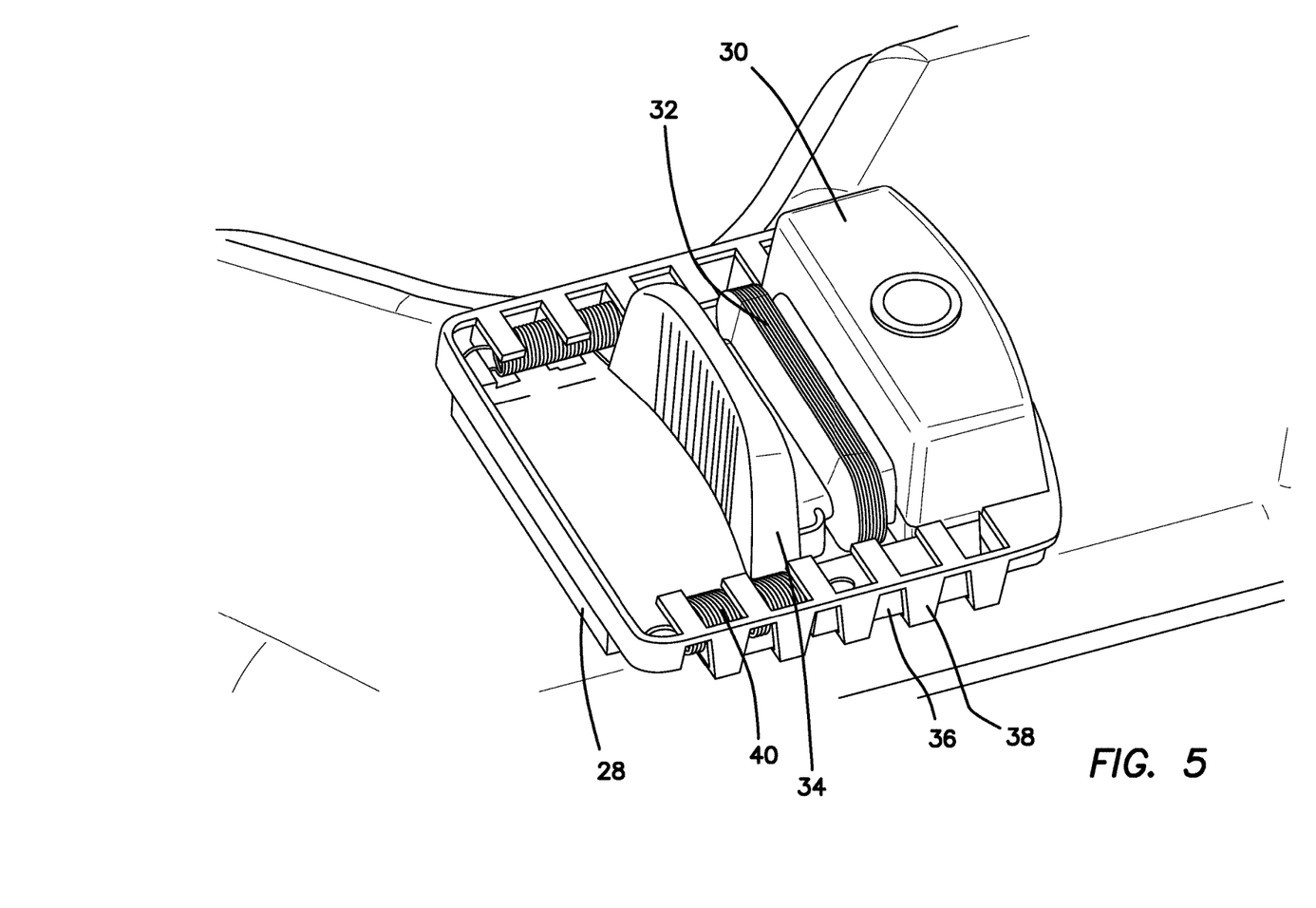
FIG. 5 is a perspective view of the vacuum hand pump disposed on the neck brace when the hand pump is in a compressed configuration.
Figure 7:
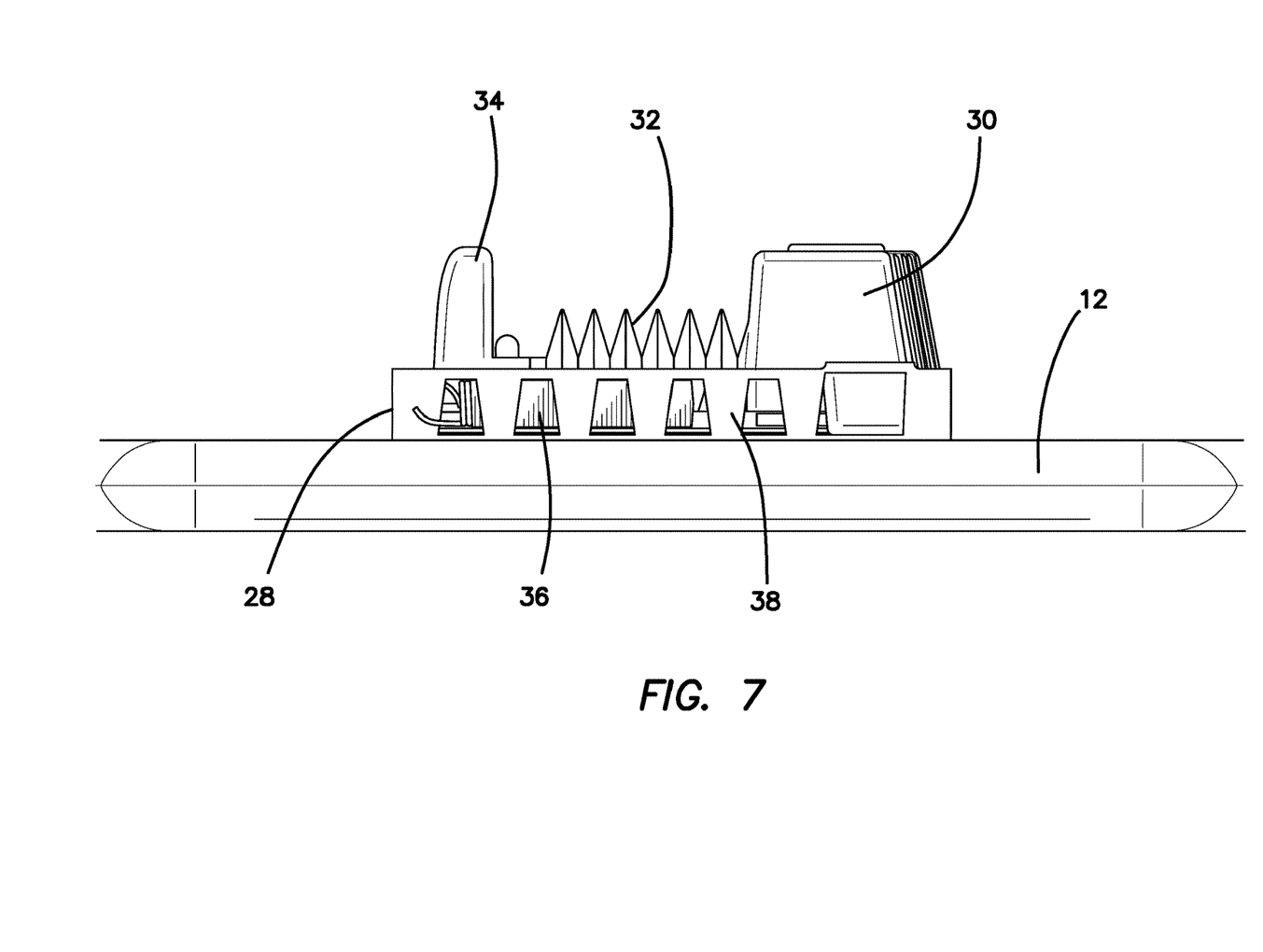
FIG. 7 is a side elevational view of the vacuum hand pump seen in FIG. 3 when the hand pump is in an expanded configuration.
Figure 8:
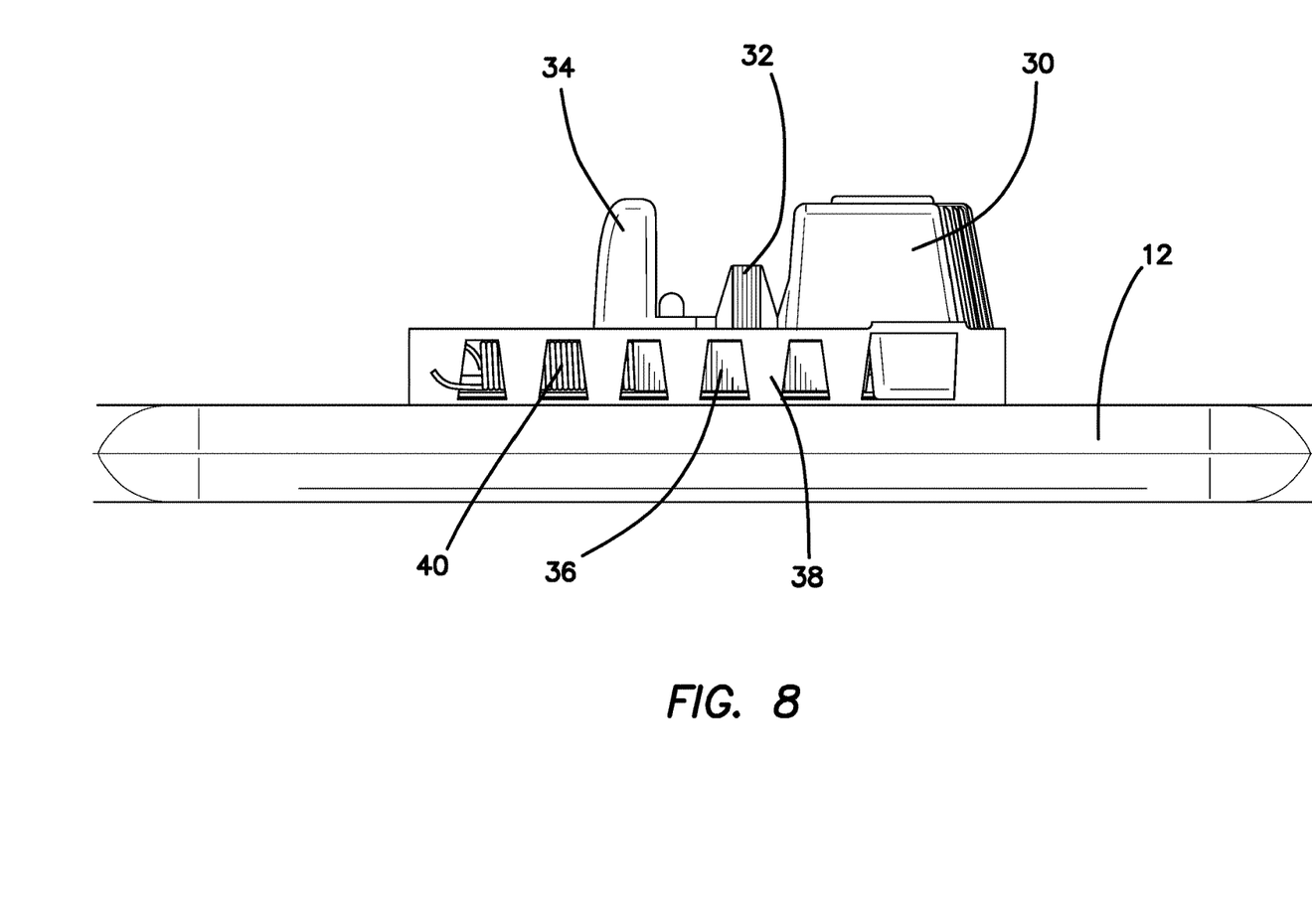
FIG. 8 is a side elevational view of the vacuum hand pump seen in FIG. 3 when the hand pump is in a compressed configuration.

After disposing the neck brace 10 around the neck of the patient and securing it in place, the user or medical professional operates the vacuum hand pump 26 by first placing his or her hand on top of the vacuum hand pump 26 seen in FIGS. 4 and 7 with the heel of his or her hand at or near the back of the housing 30 and fingers in front of the plunger 34. The user then compresses the vacuum hand pump 26 by squeezing the plunger 34 and bringing it back towards the stationary housing 30. As the user squeezes the plunger 34, the bellows 32 are compressed which drives air within the internal chamber 44 out of the housing 30 through the housing valve 42 in the direction of the arrows seen in FIG. 9. Specifically, air is driven towards the diaphragm 50 which lifts the outer circumference of the diaphragm 50 upward and off of the valve seat 48 and allowing the air to exit the housing 30. After the air pressure is equalized between the ambient environment and the internal chamber 44, the diaphragm 50 returns to its original position on the valve seat 48, thus preventing any air from reentering the internal chamber 44 of the housing 30. As the movement of the plunger 34 compresses the bellows 32, the shuttles 36 on either side of the vacuum hand pump 26 move through their respective tracks 38 and stretch each of the respective tension springs 40 coupled to each shuttle as seen in FIGS. 5 and 8.

After the bellows 32 has been fully compressed and the air driven from the internal chamber 44 of the housing 30, the user releases his or her grip on the plunger 34. The tension springs 40 then begin to compress and draw the plunger 34 away from the housing 30, thus expanding the bellows 32. The expanding bellows 32 in turn then draws air out of the body 12 of the neck brace 10 through the body valve 46 and into the internal chamber 44 of the housing 30. Once air has entered the internal chamber 44, the body valve 46 prevents its reentry back into the body 12 as is known in the art.

With air now back in the internal chamber 44 of the housing 30, the user once again may repeat the pumping process by compressing the plunger 34 and driving the air out of the housing 30 and into the ambient environment through the housing valve 42. It is in this manner that air is quickly and efficiently removed from the body 12 of the neck brace 10. With each subsequent stroke of the vacuum hand pump 26, a higher and higher vacuum is created with the body 12 which in turn removes air from the plurality of micro beads disposed within the body 12 which collapses under ambient exterior air pressure and presses the beads closer and closer together, thus making the body 12 more rigid and conforming the contours of body 12 to the shape of the patient's neck and shoulder region. The user continues to operate the vacuum hand pump 26 until the neck brace 10 is sufficiently rigidly set about the patient's neck and effectively immobilizes the patient's neck. With the neck brace 10 firmly in position, the patient may be moved as needed to receive further treatment without fear of further aggravating the patient's injuries.

To remove the neck brace 10 from the patient, the user opens a release valve 52 disposed on the back surface of the body 12 as seen in FIG. 2. The release valve 52 is a one-way valve known in the art which allows air to rush into the evacuated interior of body 12 previously pumped out by the vacuum hand pump 26. The reinserted air inflates or expands the neck brace 10 and relaxes the body 12. When the body 12 has sufficiently softened and has regained a certain amount of flexibility, the user may uncouple the ends of the body 12 from each other as disclosed above, unfold body 12 and remove the neck brace 10 from neck and shoulder region of the patient. While FIG. 2 shows the release valve 52 as being substantially disposed in a corner on the back surface of the body 12, it is to be expressly understood that this is for illustrative purposes only and that the release valve 52 may in fact be located anywhere on the front or back surface of the body 12 without significantly departing from the original intent and purpose of the current invention.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. An apparatus for immobilizing the neck of a patient comprising:
    a splint body, the splint body comprising a front surface and a back surface, a first and second end, and defining a deflatable interior;
    a coupling portion coupled to the splint body wherein the first end may be selectively joined to the second end of the splint body when the splint body is applied about the neck of the patient;
    a plurality of loosely compressible particles disposed in the deflatable interior of the splint body; and
    a vacuum hand pump coupled to the splint body and having an input communicated with the deflatable interior of the splint body, the hand pump comprising bellows, wherein the bellows are configured to be operable with a single hand,
    wherein the vacuum hand pump is configured to remove air from the deflatable interior and bring the splint body against the neck of the patient without moving the neck of the patient.

2. The apparatus of claim 1 where the vacuum hand pump comprises:
    a plunger coupled to one end of the compressible bellows;
    a housing coupled to an opposing end of the compressible bellows;
    an exhaust valve disposed in the housing; and
    a splint valve disposed within the housing,
    wherein the splint valve is communicated with the deflatable interior of the splint body.

3. The apparatus of claim 2 where the vacuum hand pump further comprises:
    a frame comprising at least one track;
    at least one shuttle disposed on a lateral side of the plunger; and
    at least one spring coupled at one end to the frame and at an opposing end to the at least one shuttle,
    wherein the at least one track is configured to accommodate the at least one shuttle there through.

4. The apparatus of claim 3 wherein the at least one spring coupled at one end to the frame and at an opposing end to the at least one shuttle is a tension spring.

5. The apparatus of claim 2 wherein the exhaust valve and the splint valve are one-way directional valves.

6. The apparatus of claim 2 wherein the housing coupled to an opposing end of the compressible bellows comprises the opposing end of the compressible bellows coupled to an internal chamber defined within the housing.

7. The apparatus of claim 6 wherein the splint valve is disposed within the internal chamber of the housing and coupled to the deflatable interior of the splint body.

8. The apparatus of claim 1 where the coupling portion is coupled to the splint body through a flexible portion disposed between the coupling portion and the splint body.

9. The apparatus of claim 1 further comprising a hook and latch fabric pad disposed on a back surface of the coupling portion and an opposing hook and latch fabric pad disposed on the front surface of the splint body.

10. The apparatus of claim 1 further comprising a release valve disposed in the splint body.

11. A method for immobilizing the neck of a patient comprising:
    coupling a neck brace comprised of a deflatable splint body having an interior filled with a plurality of compressible particles around the neck of the patient; and
    single handedly actuating a vacuum hand pump disposed on a splint body of the neck brace, wherein single handedly actuating the vacuum hand pump comprises:

pressing on a plunger with one hand, the plunger being coupled to one end of a bellows, the bellows further being coupled at an opposing to a housing;

compressing the bellows by advancing the plunger using one hand in the direction of the housing;

extending at least one spring coupled to the plunger as the bellows are compressed;

releasing the plunger;

contracting the at least one spring;

expanding the bellows as the at least one spring contracts; and removing air from the deflatable splint body of the neck brace to bring the splint body of the neck brace against the neck of the patient so that the neck brace becomes rigid about the neck of the patient without moving the neck of the patient.

12. The method of claim 11 where removing air from the splint body of the neck brace comprises drawing air from within the interior of the splint body of the neck brace into the housing of the vacuum hand pump.

13. The method of claim 12 where forcing air from a housing of the vacuum hand pump into an outside environment comprises forcing the air through a one-way directional valve disposed in the housing.

14. The method of claim 12 where drawing air from within the splint body of the neck brace into the housing of the vacuum hand pump comprises drawing the air through a one-way directional valve communicated with the interior of the splint body.

15. The method of claim 11 where compressing the bellows further comprises driving air from a housing of the vacuum hand pump into an outside environment.

16. The method of claim 11 where expanding the bellows as the at least one spring contracts further comprises drawing air from the interior of the splint body of the neck brace into the housing of the vacuum hand pump.

17. The method of claim 11 where removing air from the deflatable splint body of the neck brace to bring the splint body of the neck brace against the neck of the patient so that the neck brace becomes rigid about the neck of the patient without moving the neck of the patient comprises creating at least a partial vacuum within the interior of the splint body of the neck brace to compress the splint body of the neck brace so that the neck brace becomes rigid about the neck of a patient.

18. The method of claim 11 where coupling the neck brace around the neck of the patient comprises:

wrapping the splint body of the neck brace around the neck of the patient;

aligning a first hook and latch fabric pad disposed on a back surface of the splint body with a second hook and latch fabric pad disposed on a front surface of the splint body; and adhering the first hook and latch fabric pad to the second hook and latch fabric pad.

19. The method of claim 11 further comprising releasing the neck brace from the neck of the patient by opening a release valve disposed in the splint body of the neck brace and allowing ambient air to enter the interior of the splint body of the neck brace.

* * * * *